United States Patent [19]
Ben-Shalom et al.

[11] Patent Number: 5,965,545
[45] Date of Patent: Oct. 12, 1999

[54] COMPOSITIONS AND METHOD FOR CONTROLLING FUNGAL DISEASE IN PLANTS

[75] Inventors: Noach Ben-Shalom, Tel Aviv, Israel; David Platt, Cambridge, Mass.

[73] Assignee: State of Israel, Ministry of Agriculture, Agricultural Research Organization, The Volcani Center, Israel

[21] Appl. No.: 08/928,370

[22] Filed: Sep. 12, 1997

Related U.S. Application Data

[63] Continuation-in-part of application No. 08/730,366, Oct. 15, 1996, abandoned.

[51] Int. Cl.$^6$ .......................... A61K 31/725; A01N 43/16
[52] U.S. Cl. .............................. 514/55; 504/101; 536/20; 424/405
[58] Field of Search .............................. 514/55; 504/101; 536/20; 424/405

[56] References Cited

U.S. PATENT DOCUMENTS

| | | | |
|---|---|---|---|
| 4,536,207 | 8/1985 | McCandliss et al. | 71/88 |
| 4,946,870 | 8/1990 | Partain, III et al. | 514/777 |
| 4,970,150 | 11/1990 | Yaku et al. | 435/101 |
| 5,068,105 | 11/1991 | Lewis et al. | 424/93 |
| 5,312,908 | 5/1994 | Nakao | 536/20 |
| 5,374,627 | 12/1994 | Ito et al. | 514/55 |

FOREIGN PATENT DOCUMENTS

| | | |
|---|---|---|
| 63-2911 | 1/1988 | Japan . |

OTHER PUBLICATIONS

Gorin, P.A.J., et al., The chemistry of polysaccharides of fungi and lichens, *The Polysaccharides*, vol. 2, Academic Press, 1983, pp. 366–377.

Aldington, S., et al., Structure–activity relationships of biologically active oligosaccharides, *Plant, Cell and Environment*, 1991, 14, pp. 625–626.

Hahn, G., et al., Oligosaccharide elicitors: structures and recognition, *Mechanisms of Plant Defense Responses*, Kluwer Academic Press, 1993, pp. 99–116.

Fry, S.C., et al., Oligosaccharides as signals and substrates in the plant cell wall, *Plant Physiol.*, 1993, 103, pp. 1–5.

Hadwiger, L.A., et al., Chitosan as a component of Pea–Fusarium solani interactions, *Plant Physiol.*, 1980, 66, pp. 205–211.

Hirano, S., et al., Effects of Chitosan, Petric Acid, Lysozyme, and Chitinase on the growth of several Phytopathogens, *Agric. Biol. Chem.*, 53(11), 1989, pp. 3065–3066.

El Ghaouth, A., et al., Effect of Chitosan on Cucumber plants: suppression of *Pythium aphanidermatum* and induction of defense reactions, *The American Phytopathological Society*, 83(3), 313–320, 1994.

El Ghaouth, A., Antifungal activity of chitosan on two postharvest pathogens of strawberry fruits, *The American Phytopathological Society*, 1992, pp. 398–401.

Stossel, P., et al., Effect of Chitosan, Chitin and some Aminosugars on growth of various soilborne Phytopathogenic fungi, *Phytopath. Z.*, 111, 1984, pp. 82–90.

Kendra, D.F., et al., Characterization of the smallest Chitosan Oligomer that is maximally antifungal to *Fusarium solani* and elicits Pisatin formation in *Pisum sativum*, 1984, pp. 276–281.

Allan, C.R., The fungicidal effect of Chitosan on fungi of varying cell wall composition, *Experimental Mycology*, 3, 1979, pp. 285–287.

*Primary Examiner*—Kathleen K. Fonda
*Attorney, Agent, or Firm*—Gifford, Krass, Groh, Sprinkle, Anderson & Citkowski, P.C.

[57] ABSTRACT

Materials comprised of linked, repeat units of beta glucosamine, having a molecular weight in the range of 400 to 10,000 are highly effective in controlling fungus infestation in agricultural crops, both pre-harvest and post-harvest. The antifungal material is preferably combined with a mildly acidic solvent to produce a composition having a slightly acidic, or near neutral pH. When the antifungal material is combined with a chitosan matrix, a synergistic interaction occurs which greatly enhances the effect of the resultant composition. Also disclosed is a method for producing a chitin or chitosan based material which will dissolve in water having a neutral pH.

7 Claims, No Drawings

COMPOSITIONS AND METHOD FOR CONTROLLING FUNGAL DISEASE IN PLANTS

RELATED APPLICATION

This is a continuation-in-part of application Ser. No. 08/730,366 filed on Oct. 15, 1996 now abandoned.

FIELD OF THE INVENTION

This invention relates to agricultural compositions for controlling fungal disease in plants. Specifically the invention relates to particular carbohydrate derived compositions, and to methods for their use in preventing fungal damage to agricultural crops.

BACKGROUND OF THE INVENTION

Historically, fungal infestations have caused significant losses to agricultural crops, and have been the cause of large scale famines and economic displacements. Fungal infections can cause pre-harvest damage to crops by killing them outright or weakening them so as to decrease yields and render the plants susceptible to other infections. Post-harvest, fungal infection also results in significant loss of agricultural products during storage, processing and handling.

Clearly, there is a significant need to control the fungal infection of agricultural products, and a number of chemical agents have been developed for this purpose, but to date no fully satisfactory agents have been found. Oftentimes, fungal control agents are highly toxic to crops and/or animals; consequently, restrictions are placed on their handling and use. Also, many presently available fungal control agents are of restricted utility; that is to say, a particular agent may be only effective against several types of fungus. As a result, a number of separate materials must often be employed in a particular agricultural setting. Also, a number of species of fungus have developed resistance to commonly employed fungicides.

Clearly, there is a need for a fungal control agent for plants which has broad activity against a variety of fungi, including those strains resistant to presently employed fungicides. The material should be of low toxicity to crops and to animals, stable in composition, easy to employ and preferably low in cost.

It is known that the cell walls of fungi are comprised of chitin, which is a natural, carbohydrate-based biopolymer. Chitin is an analog of cellulose in which the OH group at the C-2 position has been replaced by an acetamido group. Chitin is also found in a number of other natural sources, including the shells of arthropods. Chitin and chitosan are polymers having relatively high molecular weights, typically several hundred thousand or more; however, they can be hydrolyzed into lower molecular weight fractions, corresponding to shortened polymer chains. Previous research has suggested that chitin, or lower molecular weight fractions produced by its degradation, can in some instances, elicit antifungal responses in some plants; see for example M. G. Hahn et al. in Mechanisms of Plant Defense Responses; B. Fritig and M. Legrand, Kluwer Academic Publishers (Netherlands 1993, pages 99–116).

Chitosan is a semisynthetic derivative of chitin produced by the deacetylation of the nitrogen thereof so as to produce the ammonium salt. Chitosan has been shown to have some mild antifungal activity with regard to certain, particular fungal species, in some particular plants; see for example, L. A. 5 Hadwiger, J. M. Beckman; Plant Physiol. 66, 205–211 (1980); A. El Gharouth et al., Phytopathology, 84, 313–320 (1994); A. El Gharouth et al., Phytopathology, 82, 398–402 (1992); C. R. Allan, et al., Experimental Mycology 3:285–287 (1979); and P. Stossel et al., Phytopathology Z., 111:82–90 (1984). Specific hydrozylates of chitosan have also been described as having some antifungal activity. See for example, Kendra et al., Experimental Mycology 8:276–281 (1984). U.S. Pat. No. 5,374,627 describes the use of a composition of a high molecular weight chitosan hydrozylate (M.W. 10,000–50,000) and acetic acid for controlling fungus in certain crops. Japanese Patent Application 62-198604 describes the use of very low molecular weight chitosan hydrozylates (M.W.≦3,000) for the control of Alternaria alternata fungus in pears. It is further noted that this material is not effective, in pears, against other fungi such as botrytis.

U.S. patent application Ser. No. 08/453,651, of Ben-Shalom et al., discloses some specific oligosaccharide materials, including materials derived from chitin and chitosan, which have antifungal activity in plants. The disclosure of that application is incorporated herein by reference.

While some fungicidal activity of chitin and chitosan derived materials has been shown or suggested in the art, such utility is limited to particular pathogens and to particular plants. Furthermore, the prior art is uncertain as to which specific materials have beneficial effect. Certain references suggest that chitosan itself is to be employed as a fungal control agent, while other references suggest that high molecular weight fractions of chitosan are effective, and other references suggest that very low molecular weight fractions must be employed.

Another problem which the prior art has encountered in connection with chitin and chitosan based materials is that these materials have a very low solubility in water. Hence, solvent systems have to be employed to solubilize them, and this limits the utility of such materials. There is a need for a method whereby these materials can be rendered soluble in water having a neutral pH.

The present invention, as will be described in detail hereinbelow, is directed to fungal control agents derived from chitin and/or chitosan. This invention has identified a particular low molecular weight fraction of chitosan derived, material which is a broad spectrum antifungal agent, effective at very low doses. The present invention has also identified particular compositions containing this low molecular weight material and chitosan, in which the material and chitosan interact, synergistically, to provide an enhanced antifungal activity. The present invention has also identified particular low molecular weight oligomers of chitin which may be employed, either alone or with other materials, as agents for fungal control. It is to be understood that the terms "oligomers" and "low molecular weight material" are to a large extent synonymous in the context of this disclosure, since both refer to relatively short polymeric chains derived by reducing the molecular weight of chitin or chitosan. For the sake of clarity, the chitosan derived materials will generally be described as "low molecular weight" materials, while the chitin derived materials will be referred to as "oligomers." However, it is to be understood that either material could be considered an oligomer or a low molecular weight material. Collectively these substances will be deemed "materials of the present invention," or "antifungal materials."

The materials of the present invention are derived from natural sources, and have extremely low toxicity to animals and agricultural crops. In addition, the materials are stable, water soluble, easy to handle and low in cost. These and other advantages of the present invention will be readily apparent from the discussion, description and examples which follow.

BRIEF DESCRIPTION OF THE INVENTION

There are disclosed herein compositions for controlling fungus disease in plants. One composition includes an antifungal material comprised of linked, beta glucosamine repeat units, having a molecular weight in the range of 4,000 to less than 10,000 daltons. The composition further includes a solvent system for the antifungal material. The solvent system comprises an aqueous solution of an acid present in an amount sufficient to provide the composition with a pH in the range of 4 to 8. In one particularly preferred embodiment, the molecular weight of the chitosan derived material is approximately 7,000 daltons, and in some embodiments, the material is present, in the solvent system, in the range of 1 to 10%. The solvent system may preferably comprise an aqueous solution of hydrochloric or an organic acid, and in a specific embodiment, the solvent comprises an aqueous solution of 0.05 to 0.5% of 14-N hydrochloric acid.

In another aspect of the present invention, there is provided another composition for the control of fungal disease in plants, which composition comprises a mixture of a chitosan matrix and an antifungal material which has a molecular weight of less than 10,000 daltons and which is comprised of linked, beta glucosamine repeat units. The material may include a low molecular weight chitosan, and this material has a molecular weight in the range of 4,000 to less than 10,000 daltons. The antifungal material may further include oligomers derived from chitin, and these oligomers may have a molecular weight in the range of 500 to 2,000 daltons. In particular embodiments, the weight ratio of chitosan to the low molecular weight and/or oligomeric material is in the range of 3:1 to 20:1. In specific embodiments, the chitosan matrix material is approximately 70% to 100% deacetylated. The mixture may further include a solvent, and the solvent may comprise an aqueous solution of an acid in an amount sufficient to give the composition a pH in the range of 4 to 8. The present invention includes a method whereby chitin and chitosan based materials may be rendered water soluble.

Also included within the scope of the present invention are methods for treating fungal disease in plants which comprise applying the compositions of the present invention to plants either pre-harvest or post-harvest.

DETAILED DESCRIPTION OF THE INVENTION

In accord with one aspect of the present invention, it has been found that materials derived from the hydrolysis of chitin or chitosan, and having a molecular weight of less than 10,000 daltons, have particular utility as a component of a fungicidal composition. This antifungal material is comprised of linked, beta glucosamine repeat units, as will be described in detail hereinbelow. The materials of the present invention are prepared by the hydrolysis of chitin or chitosan, typically by acidic or enzymatic cleavage of the polymeric material, through the oxygen linkages thereof. The exact designation of molecular weights for large, biologically derived molecules may be somewhat imprecise. Therefore, when reference is made herein to a molecular weight being "less than 10,000 daltons" it is to be understood that such term refers to all molecules whose molecular weight is anything less than 10,000, and that it excludes all molecules having a molecular weight of 10,000 or more. A similar analysis will likewise hold for other molecular weights thus specified.

One preferred antifungal material is prepared from chitosan, and comprises a 4,000 to less than 10,000 molecular weight fraction. This low molecular weight material includes a bimodal distribution of molecular weights, with a first group centered at about 4,800 daltons and a second at about 7,000 daltons. In the practice of the present invention, it has been found that the 7,000 dalton fraction is the most effective in controlling plant fungus, although the mixture is also highly effective. Another material which has utility in the present invention comprises a lower molecular weight oligomer derived from the hydrolysis of chitin. This material typically has a molecular weight in the range of about 400 to 2,000 daltons. As will be described hereinbelow, this material may be used as a fungicide by itself, or may preferably be employed in combination with other materials of the present invention.

It has further been found that the efficacy of these materials is optimized when they are disposed in an aqueous solvent containing a relatively small amount of acid. Typically, the acid is present in an amount sufficient to maintain the solution at a pH ranging from mildly acid to near neutral, typically 4–8.

Most preferably, the acid employed in the compositions of the present invention is hydrochloric acid or an organic acid. In most instances, the composition is found to be most effective as an agricultural fungicide when the pH is mildly acidic to near neutral, with a most preferred pH being 6.2 to 6.5. For certain crops, especially cereals such as wheat, a slightly acid pH, typically 4 to 5, is optimum.

The materials of the present invention are comprised of linked beta glucosamine repeat units, which are primarily joined together through their one and four positions. The basic structure of the beta glucosamine repeat unit is represented by Formula 1 hereinbelow.

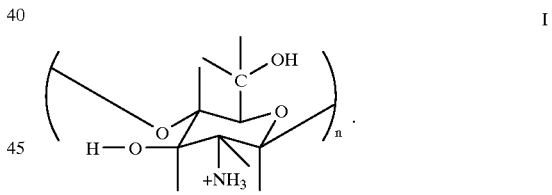

The beta glucosamine unit may, in some instances, be acetylated through the nitrogen thereof. It has been found that the material of the present invention is typically acetylated at approximately 0% to 30% of the available sites, with the remaining sites comprising the amine, which exists in a protonated form in the solution. A particular, preferred material is acetylated at approximately 5% of its sites. As noted above, one group of low molecular weight chitosan derived materials having a molecular weight in the range of 4,000 to less than 10,000 daltons have been found to have particular utility in the present invention, and chitosan derived materials with a molecular weight of approximately 7,000 daltons are particularly effective agents for controlling a variety of fungi which affect plants. In general, low molecular weight chitosans of approximately 30 to 40 repeat units have high demonstrated utility. Another group of materials which may be used in the practice of the present invention comprise oligomers of chitin having a molecular weight in the range of 400 to 2500 daltons.

The materials of the present invention may be prepared by a variety of methods, including direct synthesis. However, it has been found most economical to prepare the materials by the hydrolysis of chitin or chitosan, since these materials are readily available in large quantities, and at relatively low costs. The hydrolysis may be carried out by the use of mineral acids such as hydrochloric acid, or may be implemented by the use of enzymes such as chitosinase, which is found in commercially available hemicellulase preparations, and which is most advantageously employed in that form. In any event, the hydrolysis involves cleavage of an ether linkage joining the beta glucosamine units together. Depending upon the strength and time of reaction conditions, the molecular weight of the resultant materials may be readily controlled.

Oligomers in accord with the present invention were prepared from chitin according to the following procedure. Milled chitin (20 grams, obtained from crab shells, and provided by the Sigma Chemical Corporation) was stirred with 300 milliliters of concentrated hydrochloric acid for approximately 3 hours at 0° C. The resultant suspension of chitin was then hydrolyzed by heating the mixture to 42° C. for approximately 1.5 hours. The acidic mixture was adjusted to a pH of approximately 4.0 by the addition of potassium hydroxide. The mixture was centrifuged and the pellet discarded. The supernatant solution was passed through a membrane having a molecular weight cutoff of 20,000. The filtrate was concentrated, then desalted by utilizing a membrane having a cutoff of approximately 400 to 700 molecular weight. This resulted in a mixture of oligosaccharides, which was separated on a Bio-Gel P4 column, and the different peaks were examined by HPLC. It was found that the material included oligomers having a molecular weight in the general range of 400 to 2,500 daltons.

Low molecular weight chitosan material having a molecular weight in the range of 4,000 to 10,000 was prepared by dissolving crab chitosan, obtained from the Sigma Chemical Corporation, in 0.25% HCl. The solution was maintained at 0° for 24 hours, after which $KNO_2$ was added in a concentration of 2 mM. The reaction of the chitosan was allowed to continue for 3 hours at 25° C., and the reaction was then stopped by passing the solution through a membrane having a molecular weight cutoff of 10,000 daltons, and by increasing the pH of the solution to about 8.0 with NaOH. This caused precipitation of the hydrolyzed chitosan, which was washed several times with water and dried. This material was employed in subsequent experiments.

The antifungal materials of the present invention may be similarly prepared by enzymatic hydrolysis. In one particular preparation, 9 grams of chitosan, having a molecular weight of approximately 400,000 daltons, and obtained from the Sigma Chemical Company, was suspended in 100 milliliters of water. To this was added 100 milliliters of 0.5N hydrochloric acid, so as to solubilize the chitosan. The pH was adjusted to 5.0 by titration with 0.5N sodium hydroxide. The chitosan solution was diluted to approximately 3%, and 0.5% chitosinase, as contained in commercial hemicellulase enzyme (supplied by the Novo Chemical Company under the name Celluclast, and having up to 4 units of avicelase activity per gram of chitosan) was added. The mixture was heated to 50° C. for 5 hours. The reaction was then quenched by passing the mixture through a membrane having a molecular weight cutoff of 10,000 daltons. This removed the cellulase and any high molecular weight material. Alternatively, the reaction could be quenched by heating to 85° C. for 10 minutes, which deactivates the enzyme. As in the previous example, the resultant solution was purified by centrifuging and desalting. The product thus produced had a molecular weight in the range of 4,000 to 10,000 daltons. This mixture was separated as previously described, and examined by HPLC and found to include low molecular weight materials of approximately 4,800 daltons and approximately 7,000 daltons.

It is to be understood that the reaction conditions employed for the preparation of the materials may be readily varied by one of skill in the art, and the present invention is not limited to materials produced by any one specific method, but is directed to the low molecular weight materials and oligomeric materials of the present invention, and their utility in the treatment of fungal disease in plants.

Materials thus prepared were analyzed and characterized through gas chromatography/mass spectrometry, and nuclear magnetic resonance analysis. The 20 analysis confirmed that the main linkage in them is a 4–1 linked N-acetyl beta glucosamine. The antifungal materials also include small amounts of 3–4 and 4–6 linked N-acetyl beta glucosamines, and these linkages may represent branching. Both one-dimensional and two-dimensional NMR analyses are consistent with the structure being comprised of repeating beta glucosamine units. Molecular weight analysis of the samples was conducted by viscosity measurement as well as size exclusion chromatography, and both were consistent in their determinations.

Experimental Evaluation I

The antifungal effect of the low molecular weight chitosan of the present invention was evaluated by exposing various plant species to different fungal agents. In a general procedure, fungal cultures were grown on PDA at 20° C., and conidia from 10 day old cultures of the pathogen were collected and suspended in water containing 0.01% Tween 80 surfactant, at a concentration of $10^5$–$10^6$ cells/ml.

Pots of whole plants used in the experiment were placed on a water-containing tray and the plants kept under polyethylene bags, in an illuminated (1,200 lux) walk-in growth chamber maintained at 18° C. Test materials were applied to the plants between 48 and 72 hours before pathogen inoculation, unless otherwise noted. The plant material was inoculated with the aforementioned suspension of conidia by means of an atomizer at a volume of 1.5 ml per plant (about 50 microliters per leaf) resulting in an application of about 50–100 conidia per $cm^2$ to the plant. Unless otherwise noted, the materials were applied to the plants at approximately 1.2 mg/ml.

The plants were observed for 5 to 8 days after inoculation, and symptoms on whole plants were evaluated according to a severity index of 0–5 where 0 equals a healthy plant and 5 is a completely destroyed plant. The experiments were laid out in completely randomized, or randomized block designs, and repeated at least twice. Treatments were replicated 6 to 12 times in experiments with leaves and whole plants. Data were transformed (Arcsin), analyzed by variance analysis and tested for significance using Student-Newmand-Keul's (SNK) multiple range test.

EXAMPLE 1

This example evaluated the effect of a 0.1% solution of the chitosan material in controlling late blight disease caused in potato leaves by Phytophtora infestans. In this experiment, the leaves of the potato plants were sprayed with a 0.1% solution of the low molecular weight chitosan; and 3 days after the treated plants, and an untreated control group of plants, were inoculated with spores ($10^5$) of the fungus. The severity of the late blight disease was noted after 4 days. It was evaluated as described above, and the disease control is summarized below.

| | % Disease Control |
|---|---|
| Control | 0.0 |
| Treatment | 78.0 |

EXAMPLE 2

This example evaluated the effect of the chitosan material in controlling gray mold disease caused in cucumber leaves by Botrytis cinerea. The plants were prayed with a 0.1% solution of the chitosan material, and 3 days thereafter treated plants, and a control group, were inoculated with spores ($10^5$) of the fungus. The severity of the gray mold disease was assessed after 7 days and the results are tabulated below.

| | % Disease Control |
|---|---|
| Control | 0.0 |
| Treatment | 73.0 |

EXAMPLE 3

This experimental series assessed the effectiveness of the chitosan material in preventing gray rot disease in tomato leaves. The plants were sprayed with a 0.1% solution of the chitosan material, and 3 days thereafter the treated plants, and a control group, were inoculated with spores ($10^5$) of Botrytis cinerea. After 7 days, the severity of the disease was assessed. The results were calculated as above, and are tabulated hereinbelow.

| | % Disease Control |
|---|---|
| Control | 0.0 |
| Treatment | 75.0 |

EXAMPLE 4

This experimental series evaluated the effectiveness of the chitosan material in preventing disease caused by Botrytis cinerea in pepper fruits, post-harvest. In this experiment, peppers were injected with 40 microliters of the 0.1% low molecular weight chitosan solution, at a depth of 2 millimeters beneath the skin. Sterile water was injected into control peppers. Two days later, both groups of peppers were injected with $10^5$ spores of the fungus, in a sample volume of 30 microliters. Following infection, the fruits were stored at 20° C. for 10 days, and the appearance of rot was noted. Results of the experiment were summarized hereinbelow.

| | % Disease Control |
|---|---|
| Control | 0.0 |
| Treatment | 79.0 |

EXAMPLE 5

In this experiment, the effectiveness of the chitosan material in controlling black mold disease caused in tomato leaves by Alternaria alternata. The plants were sprayed with 0.1% of the chitosan material, and 3 days thereafter treated plants and control plants were inoculated with $10^5$ spores of the fungus. After 9 days, the severity of black mold disease was noted, and the results summarized hereinbelow.

| | % Disease Control |
|---|---|
| Control | 0.0 |
| Treatment | 72.0 |

EXAMPLE 6

This experimental series assessed the effectiveness of the chitosan material in controlling infection by Alternaria alternata in harvested pepper fruits. Peppers were harvested in the field and immersed in a 0.1% solution of the chitosan material for a period of 2 minutes. The peppers were then stored at 20° C., and development of fungal disease in treated peppers was compared with that in untreated peppers. The results are summarized hereinbelow.

| | % Disease Control |
|---|---|
| Control | 0.0 |
| Treatment | 78.0 |

EXAMPLE 7

In this experimental series, the effectiveness of the chitosan material in controlling Downey mildew disease in cucumber leaves was assessed. Plants were sprayed with 0.1% low molecular weight chitosan, and 3 days thereafter the treated plants and a control group were inoculated with fungal spores ($10^5$). The severity of the disease was assessed after 4 days, and the results of the experimental series are summarized below.

| | % Disease Control |
|---|---|
| Control | 0.0 |
| Treatment | 72.0 |

EXAMPLE 8

This experiment assessed the effectiveness of the chitosan material of the present invention in controlling disease caused in Gypsophilia paniculata (baby's breath) by Pytium fungus. The plants were sprayed with a 0.1% solution of the material, and 3 days thereafter the treated plants and a control group were inoculated with spores ($10^5$) of the fungus. The severity of the disease was examined after 4 days, and the results of the experimental series are presented hereinbelow.

| | % Disease Control |
|---|---|
| Control | 0.0 |
| Treatment | 72.0 |

It will be seen from the foregoing that the low molecular weight chitosan of the present invention are highly effective, in a variety of different plants, both pre- and post-harvest, in controlling fungal diseases caused by various organisms.

EXAMPLE 9

The 7,000 dalton molecular weight chitosan material was evaluated for fungicidal effect with regard to control of disease caused by Phytophtora Infestans in potato leaves. The composition was prepared from the approximately 7,000 dalton material in an aqueous solution of approximately. 0.1% of 14-N hydrochloric acid. The pH of the solution was approximately 6. Potato plants were sprayed with the foregoing solution, which contained approximately 1000 ppm of the material, and 24 hours later were inoculated with spores of P. infestans. A second group of substantially identical potato plants were sprayed with a control solution which comprised water and sufficient hydrochloric acid to lower the pH thereof to approximately 6. The control group was similarly inoculated, and after 5 days of incubation, the severity of disease in both groups was assessed, and the results are summarized below.

| | % Disease Control |
|---|---|
| Control | 0.0 |
| Treatment | 93.0 |

Experimental Evaluation II

While the aforedescribed chitosan derived low molecular weight materials are highly effective in controlling fungal infestations of plants, it has been found in further accord with the present invention that the antifungal effect may be greatly enhanced by employing a combination of the low molecular weight material with high molecular weight chitosan. In some instances, the mixture may also include the aforedescribed chitin derived oligomers. Specifically, it has been found that while the aforedescribed materials are highly effective fungus control agents, and while chitosan itself has been demonstrated to have some antifungal activity, a mixture of the two, preferably including a larger amount of chitosan, has a greatly enhanced antifungal effect. This result is surprising and unexpected, since there is no disclosure or suggestion in the prior art of any synergistic interaction between materials of this type.

While not wishing to be bound by conjecture, it is speculated that the chitosan may provide a matrix which supports, adsorbs, or otherwise interacts with the low molecular weight material and the oligomeric material to maintain their chemical integrity; alternatively, it is also possible that the chitosan matrix acts as a template which controls or preserves a particular morphology of the materials of the present invention which enhances their activity. It is also known that chitosan acts as a chelating agent for a number of species, and this chelation may enhance the antifungal action of the resultant mixture.

There are a number of benefits resultant from the aforedescribed discovery. Enhanced activity of the composition lowers the dosage that need be applied to a crop for fungus control. Therefore, the cost of treatment is reduced; and additionally, storing, handling and application of the material is simplified because of its enhanced potency. Additionally, chitosan is a relatively low cost, commercially available material, and since the compositions include relatively large amounts of chitosan, they are significantly lower in cost than those comprised entirely of the low molecular weight chitosan and/or chitin oligomers.

Typically, the chitosan matrix is present in a larger amount than is the low molecular weight chitosan or chitin oligomers, and it has been found that benefits of cost and efficacy are maximized when the ratio of chitosan to the other material is in the range of 3:1 to 20:1; it is to be noted that these ratios, and all other ratios and proportions given herein, are specified on a weight basis. One particularly advantageous composition comprises approximately 95% chitosan and 5% of the materials of the present invention. As in the aforedescribed material, the mildly acidic solvent system, typically comprising 0.05 to 0.5% of 14-N hydrochloric acid is utilized to fabricate the composition. In one particularly preferred group of compositions, the solvent comprises an aqueous solution of 0.1% of 14-N hydrochloric acid, and it has been found that this solvent effectively dissolves the mixture and provides a resultant composition having a pH of approximately 6.5. As noted above, organic acids may also be used as solvents, and lactic acid is another preferred acid for use in these compositions.

EXAMPLE 10

In order to demonstrate the efficacy of the chitosan matrix based mixture, a series of compositions having varying concentrations of chitosan with oligomeric material and low molecular weight material were prepared and evaluated on the basis of their ability to control gray mold disease caused by Botrytis cinerea in cucumber leaves. A series of compositions were prepared from varying proportions of the chitosan matrix with the other materials of the present invention. The chitosan was a commercially available chitosan derived from crab shells. It had a molecular weight of approximately 200,000 and is available from the Sigma Chemical Corporation. The remaining materials comprise a 50/50 mixture of chitosan derived oligomers, of the type previously described, having a molecular weight in the range of 4,000 to less than 10,000; and chitin derived oligomers, of the type previously described, having a molecular weight in the range of 500 to 2,000, hereinafter referred to as the "oligomer blend." As will be seen from Table 1 hereinbelow, the various compositions which were tested range from 100% chitosan to 100% oligomer mixture. The various compositions were sprayed, at a constant concentration, of 0.1% onto leaves of cucumber plants in accord with the procedure described hereinabove. Three days after treatment, the plants were inoculated with spores ($10^5$) of the mold. A control group of untreated plants was similarly inoculated, and the severity of gray mold disease was evaluated after 7 days. As will be seen from the table hereinbelow, a mixture comprised of 75% chitosan and 25% of the oligomer blend gave 90.2% disease control. Even when the oligomer blend decreased to 10%, 85.3% disease control was still achieved. As is illustrated by the data summarized hereinbelow in Table 10, the combination of oligomer blend and chitosan interacts synergistically to produce an enhanced effect.

TABLE 10

| Percent of Chitosan in the Mixture | Percent of Oligomer Blend in the Mixture | Percent Disease Control |
|---|---|---|
| 0.0 | 100.0 | 40.3 |
| 50.0 | 50.0 | 65.4 |
| 75.0 | 25.0 | 90.2 |
| 90.0 | 10.0 | 85.3 |
| 100.0 | 0.0 | 70.6 |

As can be seen from the foregoing, a mixture of the oligomer blend and chitosan is significantly more effective in controlling fungal disease than either of its components.

Similar results were found with regard to other plants and other fungi. In some instances, the percent of disease control achieved by the individual components will vary from that shown in Table 10, depending upon the specific plants and fungus involved; however, the synergistic effect of the components will be demonstrated with regard to various species of plants and fungi. While the foregoing experimental series employed an oligomer blend along with the chitosan matrix, similar results are found when low molecular weight chitosan is employed with the chitosan matrix.

Experimental Evaluation III

It is generally preferred that the materials of the present invention, both the low molecular weight chitosan, and the chitin oligomers as well as the chitosan matrix mixture, be employed in an aqueous solvent having a pH in the range of 4 to 8. It has been found that the effectiveness of the materials is dependent upon the pH at which they are employed. In general, the materials are most effective at a neutral to very slightly acid pH, typically in the range of 4 to 7; furthermore, effectiveness will vary with pH depending upon the particular crops to which the materials are employed.

A third experimental series was conducted to determine the effect of pH on the compositions of the present invention. This experimental series employed a chitosan/oligomer blend mixture of the type described hereinabove wherein the chitosan comprised 75% of the mixture and the oligomer blend comprised 25% of the mixture. As in the previous example, the oligomers were a 50/50 mixture of chitin derived oligomers and chitosan derived low molecular weight material. Experimental procedures and data evaluation were as previously described.

EXPERIMENT 11

In this experiment, the effect of pH on the efficacy of the chitosan oligomer blend mixture in controlling fungal disease caused by Pytium in Gypsophila paniculata was evaluated. Two samples of fungicide mixture were prepared, the first having a pH of 4.2 and the second a pH of 6.5. As in the previous example, 0.1% solutions of the material were applied to plants by spraying, and 2 days later the treated plants, and a control group, were inoculated with Pytium spores. The extent of fungal disease was evaluated after 4 days, and data from this experiment is summarized hereinbelow.

| Treatment | % Disease Control |
| --- | --- |
| Control | 0.0 |
| pH 4.2 | 85.0 |
| pH 6.5 | 45.0 |

EXAMPLE 12

In this example, the foregoing chitosan oligomer blend mixtures were evaluated for their efficacy in controlling the anthracnose disease caused by Collytotrichum in avocado fruits. The fruits were dipped, for 2 minutes, into the 0.1% solutions; and after 24 hours, spores of the fungus were sprayed onto the treated fruits, and onto a control group. The percent of disease control was evaluated after 8 days. The results are summarized hereinbelow.

| Treatment | % Disease Control |
| --- | --- |
| Control | 0.0 |
| pH 4.2 | 95.0 |
| pH 6.5 | 75.0 |

EXAMPLE 13

In this experiment, the pH dependent effect of the mixture was evaluated with regard to the control of disease caused by Botrytis cinerea in cucumbers. The plants were sprayed with the 0.1% mixtures, and 2 days later the treated plants and a control group of plants were inoculated with spores of the fungus. After 7 days, the extent of fungus disease was noted, and the results are summarized in the table hereinbelow.

| Treatment | % Disease Control |
| --- | --- |
| Control | 0.0 |
| pH 4.2 | 42.0 |
| pH 6.5 | 87.0 |

EXAMPLE 14

In this experiment, the effect of pH on the effectiveness of the chitosan oligomer blend mixture in controlling disease caused by Phytophtera infestans in potato plants. The plants were sprayed with the 0.1% solutions, and 2 days later the treated plants and a control group of plants were inoculated with fungal spores. The extent of fungus disease was evaluated after 4 days, and the results thereof are summarized hereinbelow.

| Treatment | % Disease Control |
| --- | --- |
| Control | 0.0 |
| pH 4.2 | 65.0 |
| pH 6.5 | 83.0 |

It will be seen from the foregoing examples that the effectiveness of the material of the present invention is dependent upon pH to some degree, and the optimum pH for the material will depend upon the plant on which the material is applied.

EXAMPLE 15

In this experiment, the chitosan/oligomer blend mixture was evaluated with regard to the control of late blight disease caused by Phytophtera infestans in potato leaves. A 0.1% solution of the mixture was sprayed onto the leaves, and 3 days thereafter the treated leaves and control leaves were inoculated with spores ($10^5$) of the fungus. The severity of the disease was evaluated after 4 days, and the results are summarized hereinbelow.

| | % Disease Control |
| --- | --- |
| Control | 0.0 |
| Treatment | 91.0 |

EXAMPLE 16

In this experiment, the effect of the chitosan/oligomer blend mixture in controlling gray mold disease caused by Botrytis cinerea in cucumber leaves was evaluated. The leaves were sprayed with 0.1% of the mixture, and 3 days after inoculated with spores ($10^5$) of the fungus. A control group was similarly inoculated. The severity of the gray mold disease was evaluated after 7 days, and the results of the evaluation summarized hereinbelow.

|  | % Disease Control |
| --- | --- |
| Control | 0.0 |
| Treatment | 87.0 |

EXAMPLE 17

In this experiment, the efficacy of the mixture was evaluated with regard to the control of gray mold disease caused by Botrytis cinerea in tomato leaves. The plants were sprayed with 0.1% of the mixture, and 3 days after, treated plants and control plants inoculated with spores ($10^5$) of the fungus. The severity of the gray mold disease was evaluated after 7 days, and the results summarized hereinbelow.

|  | % Disease Control |
| --- | --- |
| Control | 0.0 |
| Treatment | 83.0 |

EXAMPLE 18

In this experiment, the efficacy of the mixture was evaluated with regard to control of fungal disease caused, after harvest, in pepper fruits by Botrytis cinerea. Forty microliters of the mixture was injected 2 mm beneath the skin of red peppers. Sterile water was injected into control peppers. Two days after the peppers were injected with $10^5$ spores of the mold, in a volume of 30 microliters. The injected peppers were stored at 20° C. for 10 days, and the appearance of rot thereupon was noted. Results of the evaluation are summarized hereinbelow.

|  | % Disease Control |
| --- | --- |
| Control | 0.0 |
| Treatment | 85.0 |

EXAMPLE 19

In this experiment, efficacy of the chitosan oligomer blend mixture was evaluated with regard to the control of black mold disease caused in tomato leaves by Alternaria alternata. The tomato plants were sprayed with 0.1% of the mixture, and 3 days thereafter inoculated with $10^5$ spores of the fungus. A control group was similarly inoculated. The severity of the black mold disease was noted after 9 days. Results of the evaluation are summarized hereinbelow.

|  | % Disease Control |
| --- | --- |
| Control | 0.0 |
| Treatment | 80.0 |

EXAMPLE 20

In this experiment, the effect of the chitosan oligomer blend mixture in controlling post-harvest fungal disease caused in pepper fruits by Alternaria alternata was evaluated. The pepper fruits were harvested and dipped in a 0.1% mixture for 2 minutes and then stored at 20° C. The severity of spontaneous fungal disease in the treated peppers, as compared to untreated control peppers, was evaluated. As is summarized hereinbelow, spontaneous fungal infection in treated fruits was 83% lower than in control fruits.

|  | % Disease Control |
| --- | --- |
| Control | 0.0 |
| Treatment | 83.0 |

EXAMPLE 21

In this experiment, the effect of the mixture of the present invention in controlling Downey mildew disease caused by Pseudoperonospora cubensis in cucumber leaves was evaluated. Plants were sprayed with 0.1% of the mixture, and 3 days thereafter inoculated with spores ($10^5$) of the fungus. A control group of untreated plants was similarly inoculated. The severity of the disease was evaluated after 4 days, and the results of the evaluation represented hereinbelow.

|  | % Disease Control |
| --- | --- |
| Control | 0.0 |
| Treatment | 81.0 |

EXAMPLE 22

In this experiment, the effect of the mixture of the present invention in controlling infection of Gypsophila paniculata by Pytium was evaluated. The plants were sprayed with 0.1% of the mixture, and 3 days thereafter inoculated with $10^5$ spores of the fungus. A control group was similarly inoculated. The severity of the disease was noted after 4 days, and the results of this evaluation are summarized hereinbelow.

|  | % Disease Control |
| --- | --- |
| Control | 0.0 |
| Treatment | 84.0 |

EXAMPLE 23

In this experiment, the effect of the mixture of the present invention in inhibiting fungal anthracnose disease in avocado, caused by Collytotrichum was evaluated. The material of the present invention was applied by dipping the avocado fruits for 2 minutes into a 0.1% concentration thereof. After 24 hours, the spores of the fungus were inoculated onto the treated fruits, and onto a control group; the percent of fungal infestation was noted 8 days thereafter. Results of the evaluation are set forth below.

|  | % Disease Control |
| --- | --- |
| Control | 0.0 |
| Treatment | 95.0 |

Experimental Evaluation IV

In accord with the present invention, it has been found that the effectiveness of the compositions of the present invention is enhanced if the materials are applied to a plant prior to exposure to fungal spores. It is speculated that the materials interact with the tissues of the plant to produce an antifungal reaction which develops over time. It has also been found, however, that the materials of the present invention also exert an immediate, direct effect on spores of fungi by inhibiting their development. In this series of experiments, plant materials were treated with compositions of the present invention and inoculated with fungal spores, immediately after treatment, and some days after treatment.

EXPERIMENT 24

In this experiment, a number of Gypsophilia paniculata plants were treated with a 0.1% mixture of chitosan and oligomer blend, as previously described. A first group of treated plants were inoculated with spores of Pytium in accord with previously described protocol. A second group of treated plants were inoculated with Pytium spores after 3 days, and a control group of plants was untreated, but inoculated with spores. The extent of fungal disease was noted as previously described, and the results are summarized in the table below.

| Treatment | % Disease Control |
| --- | --- |
| Control | 0.0 |
| Day 0 | 52.0 |
| Day 3 | 93.0 |

EXPERIMENT 25

A second experiment was carried out utilizing the aforedescribed fungicidal mixture to assess the effect of incubation time on the activity of the mixture in controlling Downey mildew disease in grape leaves. Grape leaves were sprayed with the 0.1% fungicidal mixture, and then sprayed with fungal spores immediately after treatment, 3 days after treatment or 6 days after treatment. A control group was not treated, but exposed to the spores. Evaluation of the extent of fungal disease was in accord with previous protocol, and the results of the experiment are summarized in the table hereinbelow.

| Treatment | % Disease Control |
| --- | --- |
| Control | 0.0 |
| Day 0 | 61.0 |
| Day 3 | 93.0 |
| Day 6 | 100.0 |

As will be seen from the two foregoing experiments, the material of the present invention operates, over time, to elicit an antifungal response in plants. It is also believed that the material does have a direct effect against fungus, and a further experimental series was carried out to assess this effect.

EXAMPLE 26

In this experiment, $5 \times 10^5$ spores of Botrytis were mixed, in 150 microliter samples, with 0.05M glucose and 0.03M phosphate buffer, together with various concentrations of the chitosan/oligomer blend mixture. The solutions were incubated in Elisa plates for 24 hours, and vitality of the spores assessed by light microscope. As will be seen from the data below, the material of the present invention provides a dosage dependent inhibition of spore germination, in vitro, indicating that it exerts a direct inhibitory effect on fungus.

| Concentration of the Fungicide Material (PPM) | Spore Germination % |
| --- | --- |
| 500 | 0.0 |
| 125 | 0.0 |
| 31 | 0.0 |
| 8 | 80.0 |

EXAMPLE 27

In this experiment, the inhibitory effect of the mixture of the present invention was assessed for spores of Phytophtera infestans. Experimental protocol was as in Experiment 15, and the results are summarized in the table hereinbelow.

| Concentration of the Fungicide Material (PPM) | Spore Germination % |
| --- | --- |
| 500 | 0.0 |
| 125 | 0.0 |
| 31 | 0.0 |
| 8 | 80.0 |

Again, the material of the present invention produces a direct, inhibitory effect on fungal spores, which effect is dose dependent.

Therefore, acids, particularly hydrochloric acid and/or organic acids, particularly low molecular weight (C1 to C5) organic acids, are preferably employed as solvating agents in formulations of the present invention.

It is preferable that commercial formulations of the materials of the present invention be soluble in water having a near neutral pH. This eliminates the problems associated with handling acidic formulations in the field, and permits the shipping and use of a dry product which can be simply mixed with water from a conventional source In accord with another aspect of the present invention it has been, surprisingly found that when chitin, chitosan, or materials prepared thereof are dissolved in an acidic solution, and the solution subsequently evaporated to dryness, the recovered materials will be soluble in neutral water. While not wishing to be bound by speculation, it is possible that the presence of acid causes the chitin, chitosan or oligomers to maintain a molecular configuration which allows them to retain water of hydration, even after the product is evaporated to dryness.

Therefore, in accord with the present invention there has also been found a method for producing a composition for controlling fungal disease in plants, which is soluble in water having a neutral pH. The material is produced by dissolving chitin, chitosan, oligomers or other low molecular weight derivatives of chitin or chitosan, in a mildly acidic solvent, preferably an aqueous solution of hydrochloric or lactic acid, and most preferably having a pH in the range of 3–6; and subsequently removing the solvent from the solution so as to provide a dry product comprised of the foregoing chitin, chitosan or oligomers. This dry product can be subsequently redissolved in neutral water. Removal of solvent is typically accomplished by drying at elevated temperatures, although other processes such as vacuum evaporation and/or membrane based technologies may also be employed.

While the foregoing has been described with reference to some specific fungal and plant species, it is to be understood that the general principles presented hereinabove are applicable to the protection of a wide variety of agricultural crops from a broad spectrum of fungi. Also, while certain synthetic procedures for preparing the material of the present invention have been described, it is to be understood that a material may be prepared via many other routes which will be apparent to one of skill in the art. For example, other sources of chitosan or chitin may be employed for the preparation of the oligomers, and such sources include cell walls of fungi, exoskeletons of various marine invertebrates, as well as exoskeletons of terrestrial arthropods. Likewise, the chitosan matrix may be obtained from various sources. In view thereof, it is to be understood that the foregoing discussion, description and examples are illustrative of particular embodiments of the present invention, and are not meant to be limitations upon the practice thereof. It is the following claims, including all equivalents, which define the scope of the invention.

We claim:

1. A composition for controlling fungal disease in plants, said composition comprising by weight:

10–25% of an anti-fungal material selected from the group consisting of chitosan derived oligomers having a molecular weight in the range of 4,000 to less than 10,000 daltons, chitin derived oligomers having a molecular weight in the range of 500–2,000 daltons, and mixtures thereof; and 90–75% of chitosan having a molecular weight of approximately 200,000 daltons.

2. The composition of claim 1, wherein said anti-fungal material comprises a 50:50 mixture, by weight, of chitosan derived oligomers having a molecular weight in the range of 4,000 to less than 10,000 daltons and chitin derived oligomers having a molecular weight in the range of 500–2,000 daltons.

3. The composition of claim 1, further including a solvent.

4. The composition of claim 3, wherein said solvent comprises an aqueous solution of an acid, said composition having a pH in the range of 4–8.

5. A composition for controlling fungal disease in plants comprising synergistically effective amounts of:

an anti-fungal material selected from the group consisting of chitosan derived oligomers having a molecular weight in the range of 4,000 to less than 10,000 daltons, chitin derived oligomers having a molecular weight in the range of 500–2,000 daltons, and mixtures thereof, and chitosan having a molecular weight of approximately 200,000 daltons.

6. A method of controlling fungus disease in plants, said method comprising the step of applying a fungus control composition to said plants, said composition comprising:

10–25% of an anti-fungal material selected from the group consisting of chitosan derived oligomers having a molecular weight in the range of 4,000 to less than 10,000 daltons, chitin derived oligomers having a molecular weight in the range of 500–2,000 daltons, and mixtures thereof, and 90–75% of chitosan having a molecular weight of approximately 200,000 daltons.

7. A method as in claim 6, wherein said anti-fungal material comprises a 50:50 weight mixture of chitosan derived oligomers having a molecular weight in the range of 4,000 to less than 10,000 daltons, and chitin derived oligomers having a molecular weight in range of 500–2,000 daltons.

* * * * *